United States Patent
Shin et al.

(10) Patent No.: US 10,080,375 B2
(45) Date of Patent: Sep. 25, 2018

(54) COMPOSITION FOR IMPROVING BLOOD CIRCULATION AND ALLEVIATING COLD HANDS AND FEET, CONTAINING FERMENTED TEA EXTRACT

(75) Inventors: Hyun Jung Shin, Seoul (KR); Bum Jin Lee, Seoul (KR); Ji Eun Lee, Seongnam-si (KR); Yu Jin Oh, Seongnam-si (KR); Jin Oh Chung, Seongnam-si (KR); Dae Bang Seo, Yongin-si (KR); Sang Jun Lee, Seongnam-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 13/500,993

(22) PCT Filed: Oct. 15, 2010

(86) PCT No.: PCT/KR2010/007092
§ 371 (c)(1),
(2), (4) Date: Apr. 9, 2012

(87) PCT Pub. No.: WO2011/046392
PCT Pub. Date: Apr. 21, 2011

(65) Prior Publication Data
US 2012/0201805 A1 Aug. 9, 2012

(30) Foreign Application Priority Data

Oct. 15, 2009 (KR) .................. 10-2009-0098051

(51) Int. Cl.
*A61K 36/82* (2006.01)
*A61P 7/00* (2006.01)
*A23F 3/14* (2006.01)

(52) U.S. Cl.
CPC ............ *A23F 3/14* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 7,083,813 | B2 * | 8/2006 | Rosenbloom | A61K 31/121 424/725 |
| 2004/0235125 | A1 * | 11/2004 | Kottwitz | A61K 8/66 435/183 |

FOREIGN PATENT DOCUMENTS

| | | | |
|---|---|---|---|
| CN | 101107955 A | * | 1/2008 |
| CN | 101263853 A | * | 9/2008 |
| CN | 101467568 A | | 7/2009 |
| EP | 2030509 A1 | * | 3/2009 |
| JP | 10-191930 A | | 7/1998 |
| JP | 11-276072 A | | 10/1999 |
| JP | 2002-34554 A | | 2/2002 |
| JP | 2006-254837 A | | 9/2006 |
| JP | 2007-44014 A | | 2/2007 |
| JP | 2008-239504 A | | 10/2008 |
| KR | 20080066115 A | * | 7/2008 |
| KR | 10-2009-0056313 A | | 6/2009 |
| KR | 1020090056313 A | * | 6/2009 |
| WO | WO 2008/105432 A1 | | 9/2008 |

OTHER PUBLICATIONS

Ramarethinam et al. "Caffeine in tea plants: in situ lowering by Bacillus licheniformis", Indian Journal of Experimental Biology 42: 575-580, 2004.*
Kim et al. "Identification and antimicrobial activity of phenylacetic acid produced by Bacillus licheniformis isolated from fermented soybean, Chungkook-Jang", Current Microbiology 48: 312-17, 2004.*
Stangl et al. "The role of tea and tea flavonoids in cardiovascular health" Molecular Nutrition and Food Research 50: 218-28, 2006.*
Kellogg et al. "In vivo mechanisms of cutaneous vasodilation and vasoconstriction in humans during thermoregulatory challenges", Journal of Applied Physiology 100: 1709-18, 2006.*
You et al. CN101107955A (EPO machine translation).*
Yao et al. CN101263853A (EPO machine translation).*
Lee et al. KR1020090056313A (KPO machine translation).*
Chantawannakul et al. "Characterization of proteases of Bacillus subtilis strain 38 isolated from traditionally fermented soybean in Northern Thailand" Science Asia 28(4): 241-245, 2002.*
Takeo "Characteristics of the aroma constitution found in native China black teas." Agricultural and Biological Chemistry 47 (6): 1377-1379, 1983.*
Quilty-Harper "The world's fattest countries: how do you compare?", The Telegraph, Jun. 21, 2012, available online.*
Asgher et al. "A thermostable alpha-amylase from a moderately thermophilic Bacillus subtilis strain for starch processing", Journal of Food Engineering 79: 950-955, 2007.*
Lee et al. (KR 20080066115 A or appl. # KR 1020070003124) (EPO machine translation).*
Warr et al. "Seed stage development for improved fermentation performance: increased milbemycin production by Streptomyces hygroscopicus" Journal Industrial Microbiology 16: 295-300, 1996.*
Khan et al. "Targeting multiple signaling pathways by green tea polyphenol(−)-epigallocatechin-3-gallate." Cancer Research 66(5): 2500-2505, 2006 (Year: 2006).*
ShengGuorong, "The close Relationship Between Tea and Health in the Perspective of Modern Medicine," Agricultural Archaeology, No. 32, pp. 170-172, Jul. 2, 1991.
*The Cold Hand, American Society for Surgery of the Hand* (2012), <https://www.assh.org/LinkClick.aspx?fileticket=RcWIOD3V1C8%3D&portalid=1>.

\* cited by examiner

*Primary Examiner* — Emily Ann Cordas
(74) *Attorney, Agent, or Firm* — Blank Rome LLP

(57) ABSTRACT

Disclosed are a fermented tea obtained by inoculating tea with a microbial strain derived from fermented soybean sauce, and a method for producing the fermented tea. The fermented tea has superior taste and aroma, exhibits an outstanding improving effect on blood circulation and alleviating effect on cold hands and feet, and can be used various ways in the field of health foods or medical products.

7 Claims, 5 Drawing Sheets

【Figure 1】
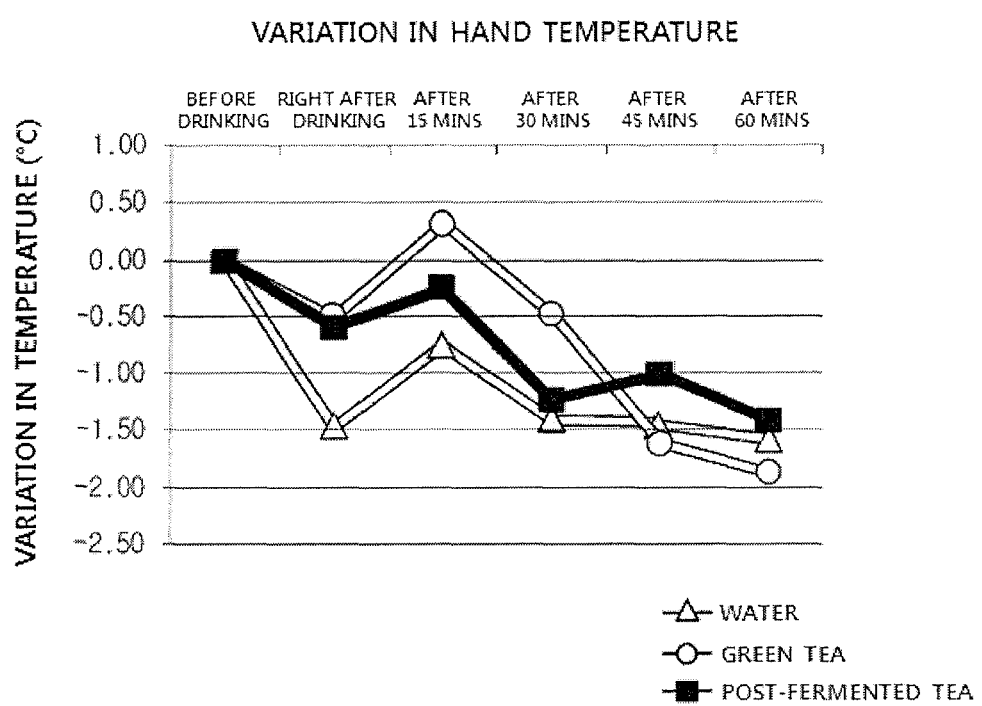

【Figure 2】
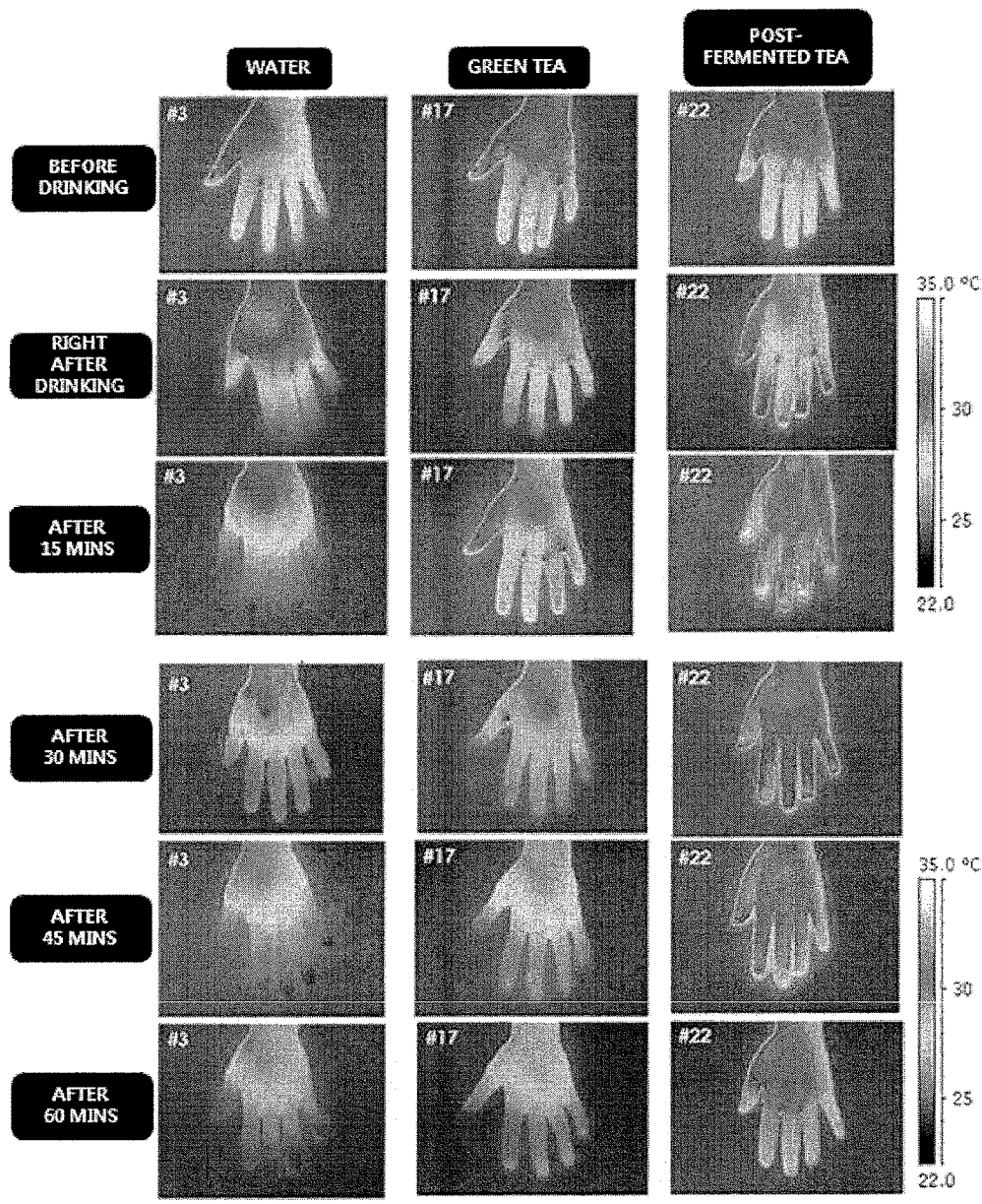

【Figure 3】
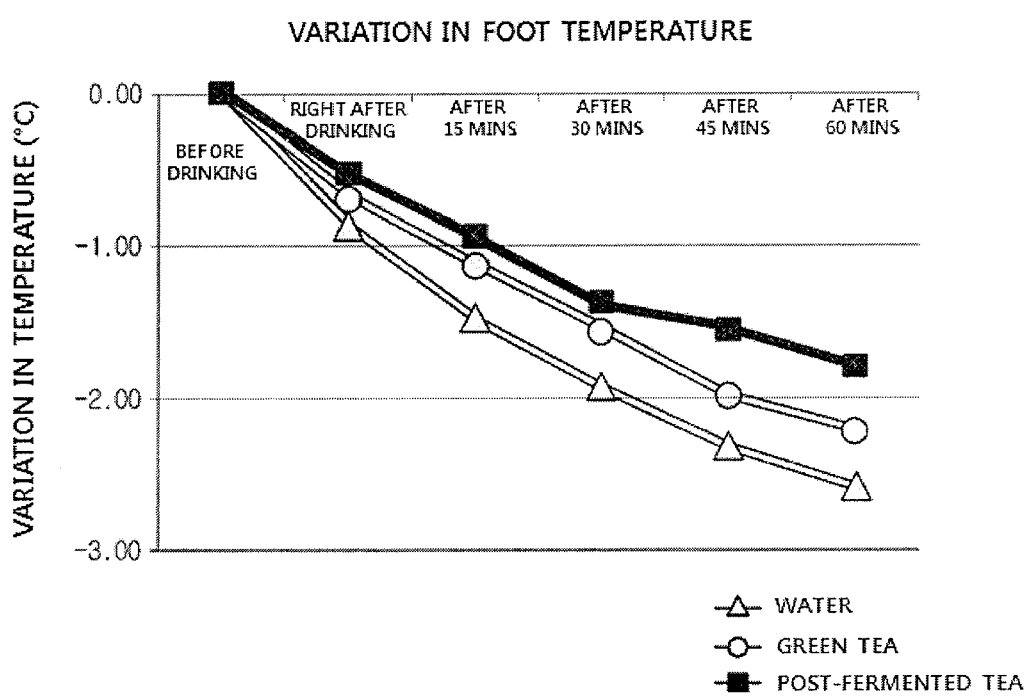

【Figure 4】
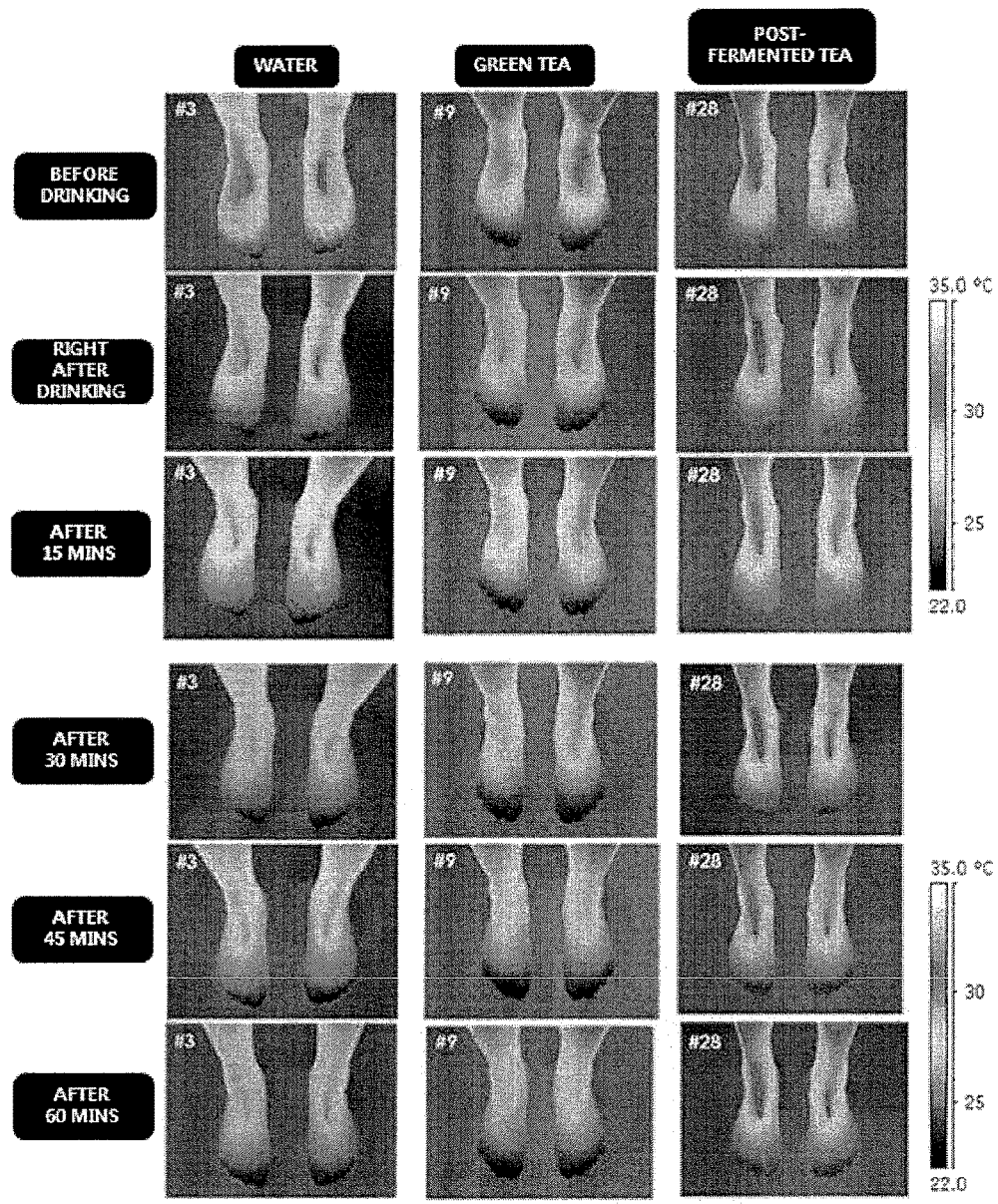

[Figure 5]
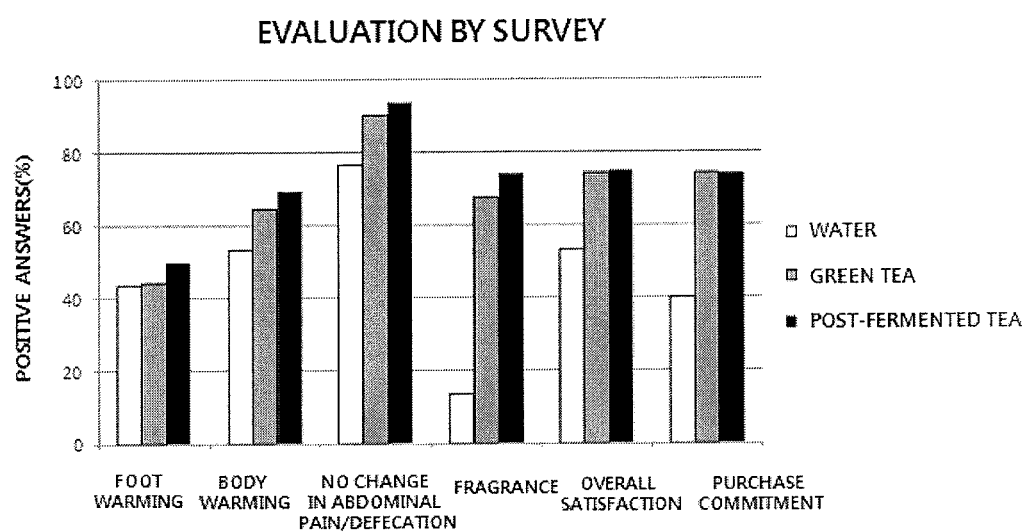

COMPOSITION FOR IMPROVING BLOOD CIRCULATION AND ALLEVIATING COLD HANDS AND FEET, CONTAINING FERMENTED TEA EXTRACT

TECHNICAL FIELD

This disclosure relates to a composition for improving blood circulation and alleviating cold hands and feet comprising fermented tea extract as an active ingredient.

BACKGROUND ART

Various kinds of tea exemplified by green tea have been known as favorite food from old times. Particularly, green tea is sometimes served for drinking in the form of tea of leaves but may be served as fermented tea in order to allow ones to enjoy deeper fragrance. For example, fermented green tea is also called different names, including green tea, oolong tea, red tea, puer tea or the like, depending on the particular type and degree of fermentation. As compared to tea of leaves, fermented tea has a different fragrance and may have an active ingredient modified to variable degrees during fermentation.

Meanwhile, modern people have more opportunities and, amount of fat intake but are living under various types of stresses. Such a change in living pattern causes various types of adult diseases, and particularly increases morbidity of circulatory system diseases, such as blood circulation disorders. Blood circulation disorders cause such conditions as hand and foot paresthesia, chronic fatigue, dizziness and pusillanimity and make it for patients to have difficulty in managing normal life. In a severe case, blood circulation disorders may proceed to various diseases, such as hyperlipidemia, arteriosclerosis, angina or the like. In general, a minor degree of blood circulation disorder may be overlooked with ease. However, as the aging process progresses, blood circulation disorders tend to become severe. Particularly, in the case of climacteric women, they increasingly suffer from hand and foot paresthesia.

The inventors of this disclosure have conducted many studies about effects of tea depending on fermentation process. Particularly, our studies focused on effective facilitation of blood circulation and alleviation of cold hands and feet.

DISCLOSURE

Technical Problem

This disclosure is directed to providing fermented tea having excellent taste and fragrance.

This disclosure is also directed to providing a composition for improving blood circulation.

This disclosure is also directed to providing a composition for alleviating cold hands and feet.

This disclosure is also directed to providing a method for preparing fermented tea.

Technical Solution

In one general aspect, there is provided fermented tea obtained by inoculating tea with a microbial strain derived from fermented soybean sauce.

In another general aspect, there is provided a method for preparing fermented tea, comprising: providing a tea-containing solution for fermentation; inoculating the solution with a microbial strain derived from fermented soybean sauce; and fermenting the inoculated solution.

Advantageous Effects

The fermented tea according to this disclosure has excellent taste and fragrance, provides an excellent effect of improving blood circulation, and may be used diversely in the field of health food or medicine.

DESCRIPTION OF DRAWINGS

FIG. 1 and FIG. 2 are a graph and an infrared photo showing variations in hand temperature with time after intake of fermented tea, respectively;

FIG. 3 and FIG. 4 are a graph and infrared photo showing variations in foot temperature with time after intake of fermented tea, respectively; and FIG. 5 is a graph illustrating the result of a survey about preference of panels after intake of fermented tea.

BEST MODE

In one aspect, there is provided fermented tea obtained by inoculating a tea ingredient with a microbial strain derived from fermented soybean sauce, followed by fermentation for a predetermined time.

There is no particular limitation in type of the tea, and examples thereof include green tea, white tea, oolong tea, red tea, puer tea, black tea, persimmon leave tea and various kinds of herb tea. According to an embodiment, the tea may be at least one selected from the group consisting of green tea, white tea, oolong tea, red tea, puer tea, black tea and persimmon leave tea. According to another embodiment, the tea may be green tea.

In addition, the microbial strain derived from fermented soybean sauce may be those derived from soy sauce, soybean paste (doenjang) or red pepper paste (gochujang) prepared by using fermented soybean lump (meju), or those derived from fast-fermented bean paste (cheonggukjang) prepared by using beans. For example, the microbial strain derived from fermented soybean sauce may be one or more strains selected from the group consisting of *Bacillus subtilis, Bacillus licheniformis, Bacillus megateriums, Bacillus natto, Bacillus citreus, Bacillus circulans, Bacillus mesentricus* and *Bacillus pumilus*. Particularly, the microbial strain derived from fermented soybean sauce may be *Bacillus subtilis*, also called hay bacillus. *Bacillus subtilis* has been used for producing amylase, protease, amino acids, antibacterial compounds or surfactants. Particularly, since *Bacillus subtilis* shows no toxicity to humans, animals and plants, it has been used widely as food microorganisms.

The "fermented tea" disclosed herein means tea in a fermented state and covers various types of tea having different tea ingredients or fermentation degrees. For example, the "fermented tea" covers all of partially fermented tea, strongly fermented tea and post-fermented tea, depending on fermentation degree.

In another aspect, there is provided a method for preparing fermented tea. The method for preparing fermented tea comprises inoculating a tea ingredient with a microbial strain derived from fermented soybean sauce, followed by fermentation for a predetermined time. Particularly, the method comprises: providing a tea-containing solution for fermentation; inoculating the solution with a microbial strain derived from fermented soybean sauce; and fermenting the inoculated solution.

There is no particular limitation in type of the tea, and examples thereof comprise green tea, white tea, oolong tea, red tea, puer tea, black tea, persimmon leave tea and various kinds of herb tea. According to an embodiment, the tea may be at least one selected from the group consisting of green tea, white tea, oolong tea, red tea, puer tea, black tea and persimmon leave tea. According to another embodiment, the tea may be green tea.

In addition, the microbial strain derived from fermented soybean sauce may be those derived from soy sauce, soybean paste (doenjang) or red pepper paste (gochujang) prepared by using fermented soybean lump (meju), or those derived from fast-fermented bean paste (cheonggukjang) prepared by using beans. For example, the Microbial strain derived from fermented soybean sauce may be one or more strains selected from the group consisting of *Bacillus subtilis*, *Bacillus licheniformis*, *Bacillus megateriums*, *Bacillus natto*, *Bacillus citreus*, *Bacillus circulans*, *Bacillus mesentricus* and *Bacillus pumilus*.

The solution inoculated with the strain may be fermented for 14 hours to 28 days. The fermentation temperature may be 20-70° C., particularly 40-60° C. When the fermentation temperature exceeds 40° C., strains other than *Bacillus subtilis* are inhibited in growth or destroyed. However, an excessively high fermentation temperature may interrupt growth of *Bacillus subtilis*.

Hereinafter, the method for preparing the fermented tea will be described in detail.

First, a solution for fermentation is inoculated with cultured *Bacillus subtilis* strain. The solution for fermentation serves as a source of water and energy for microorganisms. For example, sugar and fructose are added in an amount of 2.0-3.0 wt % based on the total weight of the solution, and soy flour may be further added thereto. Then, the solution inoculated with the strain may be cultured in an incubator in order to facilitate fermentation of the inoculated strain. After that, green tea is mixed with the solution for fermentation to provide a homogenized mixture, which, in turn, is fermented. The solution for fermentation may be used in the mixture in an amount of 10-80 wt % based on the weight of dry green tea leaves. The fermentation may be carried out in a thermostatic fermentation tank at 20-70° C. for 24 hours to 28 days. After the completion of the fermentation, the fermented tea may be further dried with hot air.

In still another aspect, there is provided extract of the fermented tea. According to an embodiment, the fermented tea may be extracted via various processes after the completion of fermentation. For example, the extract of fermented tea may be hydrothermal extract or extract using a $C_1$-$C_5$ lower alcohol, but is not limited thereto. Particularly, the extract may be hydrothermal extract. The extract of fermented tea may be formulated into various forms.

In still another aspect, there is provided a composition for improving blood circulation comprising the extract of fermented tea. For example, the composition for improving blood circulation may comprise, as an active ingredient, extract obtained by extracting fermented tea prepared by inoculating a tea ingredient with *Bacillus subtilis* strain by using various methods. The composition for improving blood circulation comprises a fermented tea ingredient using a microbial strain derived from fermented soybean sauce, and thus reduces cholesterol and triglycerides in blood sera and liver and inhibits vasoconstriction. As a result, the composition improves blood circulation, leading to improvement of conditions of hyperlipidemia or cold hands and feet.

In still another aspect, there is provided a composition for alleviating cold hands and feet comprising the extract of fermented tea. For example, the composition for alleviating cold hands and feet may comprise, as an active ingredient, extract of fermented tea obtained by inoculating green tea with *Bacillus subtilis* strain. The composition has an excellent taste and fragrance, and is effective for improving blood circulation and conditions of cold hands and feet.

In still another aspect, there is provided a food additive, health food and medicine comprising the extract of fermented tea. For example, the extract of fermented tea may be formulated into a pill, capsule, tablet, granule or drink so as to be used as health food or medicine. According to an embodiment, the fermented tea that is not subjected to a separate extraction process may be processed into the form of a liquid, powder, granule, tablet or tea bag, or into the form of tea of leaves per se. For example, fermented tea of green tea leaves may be processed into the form of a tea bag. The composition comprising the fermented tea or extract thereof is effective for reducing lipids in blood or liver, inhibiting vasoconstriction, and inducing vasorelaxation, resulting in improvement of blood circulation. For example, the composition comprising the fermented tea or extract thereof may be one for alleviating cold hands and feet.

In still another aspect, there is provided various types of food additives or functional food comprising the extract of fermented tea. For example, the extract of fermented tea may be incorporated into various additives for food, such as fermented milk, cheese, yogurt, juice, probiotics and health food, but is not limited thereto.

According to an embodiment, the extract of fermented tea may further comprise other ingredients that impart a synergic effect to a main effect to be accomplished by the present disclosure while not adversely affecting the main effect. For example, the extract may further include additives, such as fragrances, pigments, sterilizing agents, antioxidants, preservatives, moisturizers, thickening agents, inorganic salts, emulsifiers and synthetic polymer materials to improve physical properties. In addition, the extract may further include other supplementary ingredients, such as water soluble vitamins, oil soluble vitamins, polymer peptides, polysaccharides and sea weed extract. The above-listed ingredients may be selected and incorporated easily by those skilled in the art depending on particular formulation or intended use. The amount of the ingredients may be within such a range that it does not adversely affect the objects or effects of the present disclosure. For example, the ingredients may be used in an amount of 0.01-5 wt %, particularly 0.01-3 wt % based on the total weight of the composition.

The extract of the fermented tea disclosed herein may be formulated into various forms, such as solution, emulsion, viscous blend, tablets or powder. Such formulations may be administered through various methods, such as drinking, injection, spraying or squeezing.

In still another aspect, there is provided a pharmaceutical composition comprising the extract of fermented tea. The pharmaceutical composition is effective for improving blood circulation.

When applying the extract of fermented tea to medicines, the extract is used as an active ingredient and a conventional inorganic or organic carrier is added thereto to provide a solid, semi-solid or liquid formulation for oral or parenteral administration.

For oral administration, tablets, pills, granules, soft and hard capsules, dusts, fine particles, powder, emulsion, syrup, pellets or the like may be used. Meanwhile, formulations for parenteral administration include injection formulation, drops, ointment, lotion, spray, suspension, emulsion, suppositories or the like. The active ingredient disclosed herein may be formulated with ease by a currently used method. In addition, surfactants, vehicles, colorants, spices, stabilizers, preservatives, stabilizers, buffering agents, suspending agents, and other conventional adjuvants may be used in a suitable manner.

The pharmaceutical composition disclosed herein may be administered via oral, parenteral, rectal, local, transdermal, intravenous, intramuscular, intraperitoneal, subcutaneous routes, or the like.

In addition, the dose of active ingredients may be varied with the age, sex and body weight of a subject to be treated, particular disease or pathological condition to be treated, severity of disease or pathological condition, administration route and the judgment of a prescriber. Determination of the effective dose may be made by those skilled in the art based on the above-mentioned factors. In general, the effective dose may be between 0.001 mg/kg/day and 2000 mg/kg/day, particularly between 0.5 mg/kg/day and 1500 mg/kg/day.

Mode for Invention

The examples and experiments will now be described. The following examples and experiments are for illustrative purposes only and not intended to limit the scope of this disclosure.

Example 1 Preparation of Fermented Tea

First, *Bacillus subtilis* strain cultured at 30° C. for 72 hours in a vibrating incubator is recovered and separated into the strain and activated medium in a centrifugal system. The strain is cleaned three times with 1.0% physiological saline and a solution for fermentation is supplied thereto for the purpose of adequate metabolism of the microorganisms. The solution for fermentation is obtained by adding 2.5 wt % of sugar based on the total weight of the solution. Then, high-temperature pressurized sterilization is carried out under a pressure of 27 psi (pounds per square inch) at a temperature of 120° C. for 15 minutes. After the completion of sterilization, the strain is cooled at room temperature to 25° C. To facilitate fermentation metabolism of the strain damaged during the cleaning, the strain is stabilized in the solution for fermentation. Particularly, the strain cleaned three times with saline is mixed with 300 mL of the solution for fermentation before adding soybean powder thereto, and the strain is stabilized and cultured for 24 hours in an incubator.

In a sterilized reaction tank, green tea ingredients packaged into small bag units are mixed with the homogenized solution inoculated with *Bacillus subtilis* strain, and then the mixture is controlled to have a total microbial account of $10^3$-$10^8$ CFU/ml. The solution is mixed with dry leaves of green tea in an amount of 30-60 wt % based on the weight of the green tea leaves. In addition, green tea leaves are agitated continuously even after mixing them with the solution for fermentation to prevent a rapid increase in internal temperature of tea, so that the strain is not damaged by such a rapid increase in temperature. After 20 minutes during which the reaction is completed and reaction temperature is decreased, the green tea-fermentation solution mixture is sealed to prevent external air from entering through the opening, and then is subjected to fermentation. The fermentation is carried out in a thermostat fermentation tank at 60° C. for 7 days. After the completion of the fermentation, hot air drying is carried out at 80-120° C. for 5 hours to obtain fermented tea.

The fermented tea obtained by the above-described method satisfies the applicable standard of a total microbial account of $10^2$ CFU/g or less, and no pathogenic microorganisms are detected from the final product.

Example 2 Drinking Condition

The fermented tea obtained from Example 1 is weighed in a unit of 1 g and is packaged into tea bags. Then, boiling water is poured to a paper cup containing a tea bag and allowed to stand for 5 minutes. The tea bag is soaked five times and a test panel is allowed to drink tea while taking the cup with his/her right hand. A cup of tea has such an amount that it fills 80% of the volume of a currently used paper cup.

Test Example 1 Improvement of Drop in Temperature of Hands

Korean females who recognize coldness of their hands and feet are participated in the test as subjects. After they drink a sample of the fermented tea disclosed herein, their hands and feet are photographed. Based on the photos, variations in temperature of their hands are checked before and 1 hour after drinking the sample. Digital infrared thermographic imaging (DITI) includes measuring and imaging infrared rays emitted from a human body or object, and is a non-invasive photographing method providing information about a body temperature distribution on the body surface. After the completion of the test, questionnaires are given to the subjects and survey is carried out about the quality and effect of the tea sample.

Each sample is evaluated for 30 subjects. Prior to the evaluation, each subject cleans hands, and is allowed to take a rest for at least 1 hour in a space having no air movement and direct sunlight and maintaining a constant temperature-constant humidity (22° C., ~45% humidity) condition. The test is performed on the back of the left hand of each subject, and each subject is prohibited from taking a posture that may cause a change in temperature of the hand.

The hand is photographed by using an infrared camera with a distance of 60 cm from the hand and the skin emission is set to 0.98. During the photographing, any foreign material that may affect the temperature is interrupted. Photographing is carried out before and right after drinking the sample, and 15, 30, 45 and 60 minutes after drinking the sample. To prevent a change in temperature caused by the hand taking the warmed tea cup, the cup is taken by the right hand of each subject and the left hand of each subject is photographed. The drinking condition is the same as Example 2.

After the test, the data is analyzed by using REPORTER™ (Flir Co., Sweden) program which allows analysis of the skin temperature in a predetermined area. In other words, the same point on the hand is selected for each subject and the average temperature value in the area is analyzed. The temperature measured before drinking the sample is taken as the reference point '0', and the difference between the temperature before drinking the sample and the temperature after drinking the sample is calculated to show a variation in temperature. In addition, statistical significance is verified based on the control group. The test group uses the fermented tea according to Example 1 and the reference group uses non-fermented green tea.

After the lapse of a predetermined time, the results of variations in temperature is shown in FIG. 1 and IR photos are shown in FIG. 2. In FIG. 2, a darker hand color means a higher hand temperature.

Referring to FIG. 1, the control group using water as a sample shows a highest drop in temperature right after drinking the sample, and shows a continuous drop in temperature starting from the point of 15 minutes after drinking water. The reference group using green tea as a sample shows a temporary increase in temperature but shows a rapidest drop in temperature from the point of 15 minutes after drinking green tea. On the contrary, the test group using fermented tea shows the mildest drop in temperature with time.

In addition, as can be seen from FIG. 2, the test group using fermented tea shows a dark color even at the ends of fingers having a relatively low temperature. This suggests that the test group using fermented tea is prevented from a drop in temperature of hand to the highest degree. Therefore, it can be seen that the fermented tea disclosed herein prevents a drop in hand temperature, and thus is effective for alleviating cold hands and feet such chilling hands.

Test Example 2 Improvement of Drop in Temperature of Feet

Korean females who recognize coldness of their hands and feet are participated in the test as subjects. After they drink a sample of the fermented tea disclosed herein, their hands and feet are photographed. Based on the photos, variations in temperature of their feet are checked before and 1 hour after drinking the sample. Temperature measurement is carried out in the same manner under the same condition as Test Example 1.

Each sample is evaluated for 30 subjects. Prior to the evaluation, each subject cleans feet, and is allowed to take a rest for at least 1 hour in a space having no air movement and direct sunlight and maintaining a constant temperature-constant humidity (22° C., −45% humidity) condition. The test is performed on the back of both feet of each subject, and each subject is prohibited from taking a posture that may cause a change in temperature of feet.

The feet are photographed by using an infrared camera with a distance of 100 cm from feet and the skin emission is set to 0.98. During the photographing, any foreign material that may affect the temperature is interrupted. Photographing is carried out before and right after drinking the sample, and 15, 30, 45 and 60 minutes after drinking the sample. The drinking condition is the same as Example 2.

In the same manner as Test Example 1, the same point on both feet is selected for each subject and the average temperature value in the area is analyzed. The temperature measured before drinking the sample is taken as the reference point '0', and the difference between the temperature before drinking the sample and the temperature after drinking the sample is calculated to show a variation in temperature. In addition, statistical significance is verified based on the control group. The test group uses the fermented tea according to Example 1 and the reference group uses non-fermented green tea.

After the lapse of a predetermined time, the results of variations in temperature is shown in FIG. 3 and IR photos are shown in FIG. 4. In FIG. 4, a darker color at the end of a foot means a lower foot temperature.

Referring to FIG. 3, the control group using water as a sample shows a highest drop in temperature right after drinking the sample. Similarly, the reference group using green tea shows a drop in foot temperature. On the contrary, the test group using fermented tea shows the smallest drop in temperature after drinking the sample. Particularly, the test group using fermented tea shows the highest effect of maintaining temperature, 30 minutes after drinking the sample. In addition, as can be seen from FIG. 4, the test group using fermented tea shows a lightest color at the ends of feet. This suggests that the test group using fermented tea shows a smallest drop in temperature of feet.

Therefore, it can be seen that the fermented tea disclosed herein prevents a drop in foot temperature, and thus is effective for alleviating cold hands and feet such as chilling feet.

Test Example 3 Investigation of Preference after Intake of Fermented Tea

After drinking the fermented tea prepared from green tea according to Example 1, survey is carried out about the preference of subjects. The drinking condition is the same as Example 2. The questionnaire includes warming of feet and body, abdominal pain or variations in defecation after drinking, fragrance and overall satisfaction. The questionnaire also includes whether subjects would like to purchase the sample (when it is commercialized) or not. For each item, positive answers are organized, and the results are shown in FIG. 5.

Referring to the results of FIG. 5, when drinking the fermented tea disclosed herein, the subjects provide positive answers of foot warming at a higher proportion as compared to the reference group using green tea. It is also shown that the fermented tea causes abdominal pain or a change in defecation to the lowest degree. Particularly, a high portion of subjects provide positive answers about excellent fragrance. The overall satisfaction is not bad.

The composition comprising extract of fermented tea disclosed herein may be formulated into the following forms, but is not limited thereto.

Preparation Example 1 Soft Capsules

First, 100 mg of extract of fermented tea, 50 mg of extract of soybeans, 180 mg of soybean oil, 50 mg of extract of red ginseng, 2 mg of palm oil, 8 mg of hardened palm oil, 4 mg of yellow wax and 6 mg of lecithin are mixed. Then, the mixture is filled into capsules in an amount of 400 mg per capsule in a conventional manner to provide soft capsules.

Preparation Example 2 Tablets

First, 100 mg of extract of fermented tea, 50 mg of extract of soybeans, 100 mg of glucose, 50 mg of extract of red ginseng, 96 mg of starch and 4 mg of magnesium stearate are mixed. Then, 40 mg of 30% ethanol is added to the resultant mixture to form granules, which, in turn, are dried at 60° C. and formed into tablets by using a press.

Preparation Example 3 Granules

First, 100 mg of extract of fermented tea, 50 mg of extract of soybeans, 100 mg of glucose, 50 mg of extract of red ginseng and 600 mg of starch are mixed. Then, 100 mg of 30% ethanol is added to the resultant mixture to form granules. The granules are dried at 60° C. and packed into bags. The final content is set to 1 g.

Preparation Example 4 Drink

First, 100 mg of extract of fermented tea, 50 mg of extract of soybeans, 10 g of glucose, 50 mg of extract of red ginseng, 2 g of citric acid and 187.8 g of purified water are mixed to provide a drinking solution, which, in turn, is filed into a bottle. The final volume is set to 200 mL.

The invention claimed is:

1. A method for improving blood circulation and alleviation of cold hands and feet of a subject in need thereof, comprising:

providing a solution for fermentation;
adding sugar or fructose to the solution;
inoculating the solution with *Bacillus subtilis*;
stabilizing the *Bacillus subtilis* by culturing the *Bacillus subtilis* before adding green tea to the fermentation solution;
mixing the inoculated solution with green tea leaves, wherein the *Bacillus subtilis* is in an amount of $10^3$ to $10^8$ CFU/ml, and the green tea leaves are in an amount of 30-60 wt % based on the total weight of the solution;
fermenting the inoculated solution at a temperature of above 40° C. but less than or equal to about 60° C. for 24 hours to 28 days to provide a fermented green tea; and
administering to the subject an effective amount of the fermented green tea to improve blood circulation and alleviates cold hands and feet of the subject.

2. The method of claim 1, wherein the effective amount is between 0.001 mg/kg/day and 2000 mg/kg/day.

3. The method of claim 2, wherein the effective amount is between 0.5 mg/kg/day and 1500 mg/kg/day.

4. The method of claim 1, wherein the *Bacillus subtilis* is stabilized by culturing the *Bacillus subtilis* for 24 hours.

5. The method of claim 1, wherein the *Bacillus subtilis* is a microbial strain derived from fermented soybean sauce.

6. A method for alleviating cold hands and feet of a subject, comprising:

providing a solution for fermentation;
adding sugar or fructose to the solution;
inoculating the solution with *Bacillus subtilis*;
stabilizing the *Bacillus subtilis* by culturing the *Bacillus subtilis* before adding green tea to the fermentation solution;
mixing the inoculated solution with green tea leaves, wherein the *Bacillus subtilis* is in an amount of $10^3$ to $10^8$ CFU/ml, and the green tea leaves are in an amount of 30-60 wt % based on the total weight of the solution;
fermenting the inoculated solution at a temperature of above 40° C. but less than or equal to about 60° C. for 24 hours to 28 days to provide a fermented green tea; and
administering to the subject an effective amount of a fermented green tea that alleviates cold hands and feet of the subject.

7. A method according to claim 6, wherein the fermented green tea comprises *Sinensis Forma bohea*.

* * * * *